United States Patent [19]

Nakaguchi

[11] Patent Number: 5,256,678
[45] Date of Patent: * Oct. 26, 1993

[54] NORMAL-PENTADECYL NICOTINATE N-OXIDE AND HAIR RESTORER COMPRISING THE SAME

[75] Inventor: Osamu Nakaguchi, Toyonaka, Japan

[73] Assignee: Fujisawa Pharmaceutical Co., Ltd., Osaka, Japan

[*] Notice: The portion of the term of this patent subsequent to Jun. 18, 2008 has been disclaimed.

[21] Appl. No.: 886,803

[22] Filed: May 22, 1992

[30] Foreign Application Priority Data

May 27, 1991 [JP] Japan ............................ 3-225433

[51] Int. Cl.$^5$ .................. A61K 31/425; C07D 213/89
[52] U.S. Cl. ...................................... 514/356; 546/318
[58] Field of Search ......................... 546/318; 514/356

[56] References Cited

U.S. PATENT DOCUMENTS

| 2,431,558 | 11/1947 | Huber | 514/279 |
| 4,847,260 | 7/1989 | Abe et al. | 514/279 |
| 5,025,026 | 6/1991 | Osamu | 514/356 |

FOREIGN PATENT DOCUMENTS

| 0346490 | 12/1989 | European Pat. Off. | |
| 0408203 | 1/1991 | European Pat. Off. | 546/318 |

OTHER PUBLICATIONS

Patent Abstracts of Japan, (9112) May 16, 1985 & JP-A-60 004 113 (Raion KK) Jan. 10, 1985.

Primary Examiner—C. Warren Ivy
Assistant Examiner—Zinna N. Davis
Attorney, Agent, or Firm—Oblon, Spivak, McClelland, Maier & Neustadt

[57] ABSTRACT

This invention relates to n-pentadecyl nicotinate N-oxide, a hair restorer composition comprising said compound as the active ingredient and a method of hair restoring utilizing said compound.

3 Claims, No Drawings

NORMAL-PENTADECYL NICOTINATE N-OXIDE AND HAIR RESTORER COMPRISING THE SAME

The present invention relates to n-pentadecyl nicotinate N-oxide, which is a novel compound of the formula:

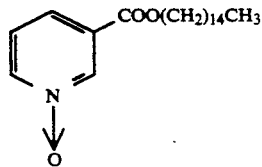

and has a hair restorative action, and to a hair restorer comprising the same.

A hair restorative action has been reported in esters of aliphatic alcohols containing an odd number of carbon atoms with aliphatic carboxylic acids, succinic acid, citric acid, fumaric acid, lactic acid, pyruvic acid, malic acid, oxaloacetic acid or phosphoric acid (Japanese Patent Publication Kokai No. 4113/1985).

The inventor of this invention has already found that n-pentadecyl nicotinate has a potent hair restorative action (Japanese Patent Publication Kokai No. 250310/1989, U.S. Pat. No. 5025026).

However, the hair restorative action of the above-mentioned esters of aliphatic alcohols containing an odd number of carbon atoms is not sufficiently potent and none of them have ever been put to use.

The inventor of this invention found that n-pentadecyl nicotinate N-oxide, which is obtainable by oxidizing the above-mentioned n-pentadecyl nicotinate, has an outstandingly potent hair restorative action as compared with the esters of aliphatic alcohols containing an odd number of carbon atoms as disclosed in Japanese Patent Publication Kokai No. 4113/1985 and that said N-oxide is superior in hair restorative action even when compared with the n-pentadecyl nicotinate described in Japanese Patent Publication Kokai No. 250310/1989. The inventor has implemented the above findings into this invention.

Said n-pentadecyl nicotinate N-oxide of this invention can be prepared by oxidizing n-pentadecyl nicotinate in the conventional manner using an oxidizing agent.

As suitable examples of the oxidizing agent, there may be mentioned inorganic peracids or salts thereof (e.g. periodic acid, persulfuric acid, etc., sodium and potassium salts thereof), organic peracids or salts thereof (e.g. perbenzoic acid, 3-chloroperbenzoic acid, performic acid, peracetic acid, chloroperacetic acid, trifluoroperacetic acid, etc., sodium or potassium salts thereof, etc.), ozone, hydrogen peroxide, and urea-hydrogen peroxide, among others.

The hair restorer according to this invention comprises n-pentadecyl nicotinate N-oxide as an active ingredient.

The hair restorer of this invention is manufactured by formulating n-pentadecyl nicotinate N-oxide with a varying type of base such as an emulsion base, cream base, lotion base or hair tonic base in the per se conventional manner. The concentration of n-pentadecyl nicotinate N-oxide in such varied formulations is not restricted but is appropriately in the range of about 0.1 to 10 percent by weight for all practical purposes.

The hair restorer of this invention produces a synergistic effect when it contains, in addition to n-pentadecyl nicotinate N-oxide, such other active ingredients as carpronium chloride, swertia herb extract, vitamin E nicotinate, capsicum tincture, etc. which have cutaneous peripheral vasodilating activity.

The following test example is intended to illustate the efficacy of the hair restorer of this invention which contains n-pentadecyl nicotinate N-oxide.

TEST EXAMPLE

Method

Groups of 10 C$_3$H mice (HeNCrj; 42 days old) were acclimatized for 8 days and used as test animals. Before 3 days on the start of the application of test solution, the back of each mouse was shaved with a razor to thereby expose a skin area of 4 cm × 2 cm.

Starting from the 51st day of age, namely while the mice were not in the hair growth period, the test solution was applied to the shaved area of the back of each mouse once every day except Sundays at a dose of 0.1 ml per day. On the 7th day of application and thereafter, the condition of the shaved skin area was observed macroscopically and photographically at 3-day intervals and rated on the following 5-point scale:

|  | Score |
|---|---|
| The skin has a pink color | 1 |
| Color change to gray in less than 50% of the shaved skin area | 2 |
| Color change to gray in not less than 50% of the shaved skin area | 3 |
| Hair growth observable in less than 50% of the shaved skin area | 4 |
| Hair growth observable in not less than 50% of the shaved skin area | 5 |

Test Solutions (1) 1% Solution of n-pentadecyl nicotinate N-oxide in ethanol
(2) n-Pentadecanoic acid glycerol ester preparation (control)
(3) 99.5% Ethanol (control)

Results

| | Total score of 10 mice after start of test solution application | | | | | | | |
|---|---|---|---|---|---|---|---|---|
| | Day 0 | Day 7 | Day 10 | Day 13 | Day 16 | Day 19 | Day 22 | Day 25 |
| (1) | 10 | 18 | 25 | 43 | 50 | — | — | — |
| (2) | 10 | 10 | 15 | 18 | 39 | 46 | 50 | — |
| (3) | 10 | 10 | 12 | 14 | 19 | 24 | 31 | 33 |

The above test results clearly indicate that the active ingredient of this invention, namely n-pentadecyl nicotinate N-oxide, has a potent hair restorative action.

EXAMPLE 1

(1) Synthesis of n-Pentadecyl Nicotinate

Nicotinic acid (123 g) and dichloromethane (861 g) are placed in a flask, thionyl chloride (120 g) is then added dropwise at 30°±5° C. over 1 hour, and the resulting mixture is stirred for 8 hours.

A mixture of n-pentadecanol (228 g) and dichloromethane (520 g) is then added to the above mixture at 30°±5° C. over about 1 hour, followed by 12 hours of stirring.

The reaction mixture is neutralized by addition of sodium hydroxide (200 g) and ice water (2,500 g). The organic layer is separated, washed with water, dried over magnesium sulfate, and concentrated.

The residue is treated with 95% ethanol (1,500 g) and activated carbon (50 g) with warming and then filtered. The filtrate is allowed to stand in a refrigerator for recrystallization. n-Pentadecyl nicotinate (183 g) is thus obtained.

Melting point: 35° C.

(2) Synthesis of n-Pentadecyl Nicotinate N-oxide n-Pentadecyl nicotinate (27 g) obtained as described in (1) and acetic acid (200 g) are placed in a flask. While the flask contents are maintained at 80°±5° C., 35% aqueous hydrogen peroxide (30 g) is added dropwise thereto over 30 minutes and the reaction is then continued for 8 hours.

After completion of the reaction, the reaction mixture is poured into ice water containing sodium hydroxide. Extraction with dichloromethane, washing with water, drying and concentration give crude crystals. Recrystallization using toluene (58 g) and activated carbon (5 g) gives n-pentadecyl nicotinate N-oxide (19 g).

IR (Nujol): 1721, 1607, 1493 cm$^{-1}$.

Mass spectrum: M$^+$ 350.

NMR (CDCl$_3$, δ): 0.876 (t, 3H, J=7.4 Hz), 1.263 (bs, 26H), 4.35 (t, 3H, J=7 Hz), 7.408 and 7.322 (dd, 1H, H=7.6 Hz), 7.856 (d, 1H, J=8 Hz), 8.336 (d, 1H, J=8 Hz), 8.778 (s, 1H).

EXAMPLE 2 n-Pentadecyl nicotinate N-oxide as obtained in Example 1 is dissolved in 99.5% ethanol to provide a 1% solution.

EXAMPLE 3

| | |
|---|---|
| n-Pentadecyl nicotinate N-oxide | 3.0% by weight |
| Carpronium chloride | 1.0 |
| 95% Ethanol | 80.0 |
| Purified water | 15.5 |
| Perfume, colorant and preservative | q.s. |

A lotion is produced by adding n-pentadecyl nicotinate N-oxide and carpronium chloride to 95% ethanol and further adding purified water, perfume, colorant and preservative with stirring to effect dissolution.

EXAMPLE 4

| | |
|---|---|
| (Phase A) | |
| n-Pentadecyl nicotinate N-oxide | 1.0% by weight |
| Cetanol | 2.0 |
| Petrolatum | 5.0 |
| Glyceryl trioctanoate | 10.0 |
| Polyoxyethylene monostearate | 2.0 |
| (Phase B) | |
| Glycerin | 10.0% by weight |
| Purified water | 69.5 |
| Perfume, colorant and preservative | q.s. |

An emulsion is produced by melting the phase A components by heating at 80° C., then adding the phase B components heated at 80° C. to the phase A, stirring the mixture to effect emulsification, and cooling the same to ambient temperature.

What is claimed is:

1. n-Pentadecyl nicotinate N-oxide.

2. A hair restoring composition comprising an effective amount of n-pentadecyl nicotinate N-oxide as the active ingredient, in admixture with a pharmaceutically acceptable carrier.

3. A method of restoring hair in a subject in need thereof, which comprises administering to the subject an effective amount of n-pentadecyl nicotinate N-oxide.

* * * * *